(12) United States Patent
Brown (10) Patent No.: US 6,482,356 B1
(45) Date of Patent: Nov. 19, 2002

(54) METERED LUBRICANT DISPENSER FOR DENTAL HANDPIECES

(76) Inventor: Kenneth R. Brown, 11402 N. 69th St., Scottsdale, AZ (US) 85254

( * ) Notice: Subject to any disclaimer, the term of this patent is extended or adjusted under 35 U.S.C. 154(b) by 0 days.

(21) Appl. No.: 09/498,463

(22) Filed: Feb. 4, 2000

(51) Int. Cl.[7] ............................................... C23F 11/00
(52) U.S. Cl. ................. 422/1; 252/10; 422/7; 422/26; 422/27; 422/28; 422/40; 433/104; 134/94.1; 134/100.1
(58) Field of Search .......................... 422/26, 27.7, 28, 422/297, 40, 110, 300; 134/94.1, 100.1; 433/104

(56) References Cited

U.S. PATENT DOCUMENTS

| | | | |
|---|---|---|---|
| 4,990,087 A | * | 2/1991 | De Rocchis et al. ......... 433/104 |
| 5,520,882 A | * | 5/1996 | Brown ........................... 422/7 |
| 5,723,090 A | * | 3/1998 | Beerstecher et al. .......... 422/26 |

* cited by examiner

Primary Examiner—Krisanne Thornton
(74) Attorney, Agent, or Firm—Gregory J. Nelson (57) ABSTRACT

A pump is supported on a housing and has an inlet port coupled to a lubricant supply and an outlet port coupled to a tube outlet opening for delivering a predetermined amount of the lubricant during an activated cycle of the pump. An actuator, when triggered, operates in an actuated state for a predetermined duration during which time the pump is activated for one cycle and delivers a predetermined amount of the lubricant to the tube outlet opening. A switch is independently selectable for triggering the actuator to activate only the active cycle of the pump. The actuator may be a spring-biased solenoid or a timer circuit with a relay. The pump may be a piston-diaphragm type or any one of various motor driven types. The pump is activated for about 1 second, without also activating a cleaning cycle or a purging cycle and delivers ⅛ to ½ cc of a lubricant comprising about 90% by volume of a pharmaceutical grade mineral oil and about 10% by volume of NNL-690. The duration of the active cycle is adjustable and controls the amount of lubricant delivered by the pump. The lubricant is delivered at a pressure of about 2.6 psi well into the air intake hole of the handpiece while holding the handpiece upside down so as to assure that a maximum amount of the lubricant is delivered as near as possible to and reaches and remains in the handpiece rotor assembly to enable the formation of an effective eutectic film during a subsequent sterilization step.

25 Claims, 5 Drawing Sheets

METERED LUBRICANT DISPENSER FOR DENTAL HANDPIECES

BACKGROUND OF THE INVENTION

1. Fields of the Invention

The present invention relates generally to an apparatus and method of lubricating dental handpieces and, more particularly, to a dispenser which delivers an accurately metered amount of dental handpiece lubricant to the turbine rotor and bearings of the handpiece prior to sterilization.

2. Discussion of Background and Prior Art

Heretofore three methods have been used to dispense lubricants into a dental handpiece prior to sterilization as follows:

1 In a method by Brown in U.S. Pat. No. 5,520,882 ("the Brown '882 patent") there is described and claimed a dental handpiece lubricant that includes about 90% by volume of a liquid hydrocarbon and about 10% by volume of a lubricant enhancer and corrosion inhibitor, such as, NNL-690, which forms a eutectic film over the rotor bearings during the subsequent sterilizing step and extends handpiece life and is sold by Steri-Lube International, Ltd under the brand name Steri-Lube™.

Figure 1:
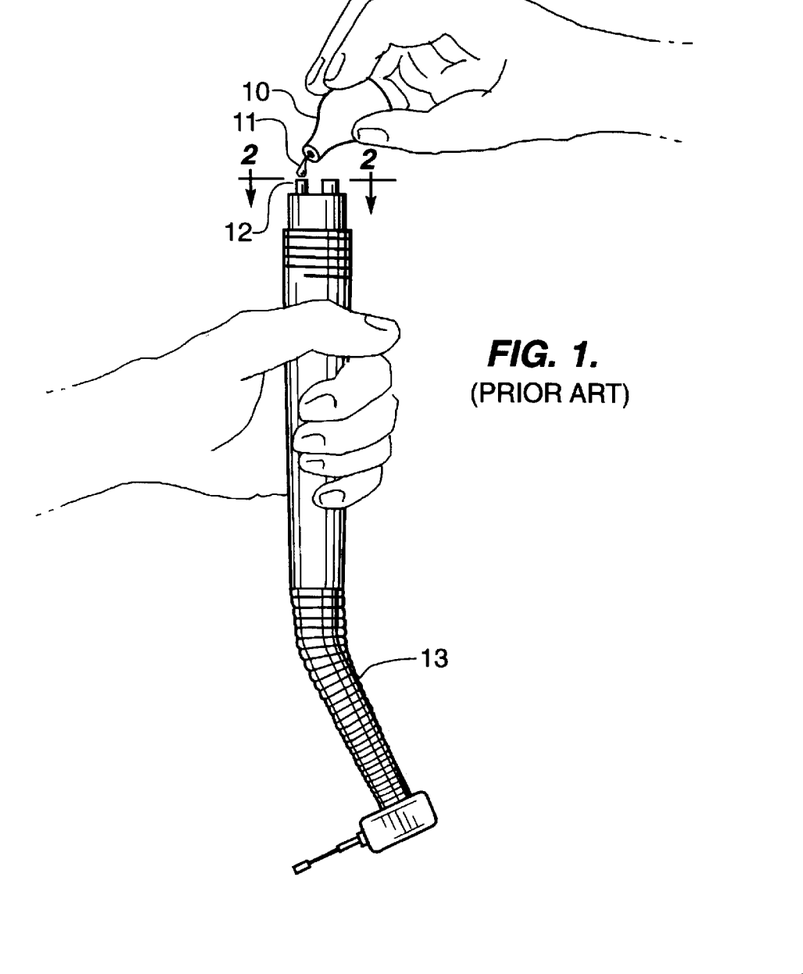
FIG. 1 is a perspective view of the prior method taught by the Brown '882 patent of dispensing the Steri-Lube™ lubricant into the air intake hole of the handpiece.
Figure 2:
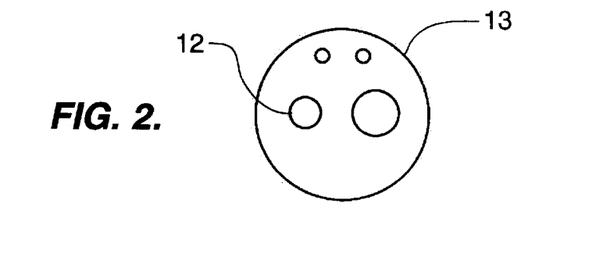
FIG. 2 is a plan view of the air intake hole of the handpiece of FIG. 1.

The Brown '882 patent is hereby incorporated herein by reference. The Brown '882 patent describes a method in which a small packet 10 containing a pre-measured amount of Steri-Lube™ lubricant is squeezed to empty the packet contents 11 into the air intake hole 12 of the handpiece 13 while holding the handpiece upside down as seen in FIGS. 1, 2 of the present application. While the method described in the Brown '882 patent delivers an accurate dose of the lubricant to the aft handpiece rotor assembly, the process is time consuming and clumsy, and the amount of lubricant that actually reaches the turbine rotor assembly varies from use to use depending on who performs the step and how it is performed.

2 Another prior method is performed by inverting a drop bottle containing the lubricant and squeezing the lubricant out through a needle attached to the bottle outlet opening and placing the drops into the air intake opening of the handpiece. This procedure does not deliver an accurate dose to the rotor assembly.

3 The third method is performed by dispensing the lubricant from a pressurized canister with a nozzle tip into the handpiece air intake opening and expelling the excess lubricant. This procedure not only does not deliver an accurate metered dose of the lubricant to the rotor assembly, but also, as described in greater detail below, reduces the ability of a lubricant enhancer and corrosion inhibitor lubricant, such as, Steri-Lube lubricant, to form its eutectic film over the handpiece rotor bearings during the subsequent autoclave step.

Accordingly, it is an object of the present invention to quickly (i.e., less than 1 second), simply (i.e., just push a button), accurately (i.e., +/−10% stroke-to-stroke, +/−2 microliters with linear actuator), and efficiently (i.e., virtually all of the lubricant goes to and remains at the rotor assembly) dispense a predetermined dose (i.e., ⅛–½ ccs) of a dental handpiece lubricant onto the moving parts of a dental handpiece.

Prior Assistina™ Cleaning, Lubricating, and Purging System

The prior Assistina™ Model 301 Plus system made by W&H Dentalwerk Burmoos, A-5111 Burmoos, Austria, and distributed in the United States by A-DEC International, Inc., 2601 Crestview Drive, Newberg Oreg. 97132, automatically cleans, lubricates, and purges a dental handpiece prior to sterilization. In operation the spay air and spray water channels of the dental handpiece are connected via an adaptor to a 65 psi to 140 psi compressed air supply line which is apparently stepped down to an unspecified operating pressure level by an in line regulator. (It is noted that a typical air handpiece operates at 30–35 psi.) The connected handpiece is then placed in a cigar-shaped holder which is then placed into an operating chamber in the unit and a lid is closed to cover the chamber. Pressing and holding the start button for 2 seconds initiates a timed 35 second cycle which, in pre-programmed, non-selectable, automatic sequence, first flushes cleaning fluid through the spray air and spray water channels, then injects a metered dose of ordinary service oil to lubricate the internal working parts of the handpiece, and then finally purges the handpiece by applying compressed air to blow the spray air and spray water channels free of the cleaning solution and the internal moving parts free of any excess oil. It is estimated that the minimum pressure needed to overcome inertia and spin the turbine rotor sufficiently fast to throw off the excess oil is not less than about 25 psi. The unit comes with two universal adaptors for maintaining more than one handpiece type.

There are many problems with this unit including: (1) it is very expensive, retailing for about $1,820.00 at the time of filing the present application; (2) it is very slow (35 seconds) and complex (3 operations in every cycle); (4) the individual operations are not independently selectable by the user, but rather come bundled as an automatic preprogrammed sequence; (5) it does not disclose or suggest dispensing a dental handpiece lubricant, such as the Steri-Lube™ lubricant, that includes about 90% by volume of a liquid hydrocarbon and about 10% by volume of a lubricant enhancer and corrosion inhibitor, such as, NNL-690, which forms a eutectic film over the rotor bearings during the subsequent sterilizing step; (6) the mandatory cleaning step destroys much of the remaining eutectic film built up over the rotor bearings as a result of any previous use prior to sterilization of a lubricant enhancer and corrosion inhibitor type lubricant, such as, the Steri-Lube™ lubricant; and, (7) the mandatory purging step blows out the excess lubricant using an unspecified, but inherently high, air pressure (estimated at 25 psi minimum to 35 psi maximum) prior to the sterilizing step to prevent over-oiling, thereby removing a significant portion, if not virtually all, of the excess lubricant, which step would deprive a lubricant enhancer and corrosion inhibitor type dental handpiece lubricant, such as Steri-Lube™, from having a sufficient dose of the lubricant to form an optimal, long lasting eutectic film under the heat of the subsequent autoclave even if such a lubricant enhancer and corrosion inhibitor type lubricant, such as, the Steri-Lube™ lubricant, were to be used therein.

Accordingly, it an object of the present invention to dispense the measured amount of the dental lubricant to the rotor turbine assembly during each application without first cleaning or purging prior to sterilization.

It is a further object of the present invention to dispense a lubricant enhancer and corrosion inhibitor type lubricant, such as, the Steri-Lube™ dental handpiece lubricant, into the air intake line of a dental handpiece by metering the measured amount of said lubricant under such circumstances (2.6 psi while holding the handpiece upside down and using a long needle nosed tip) as to assure that a sufficient supply of said lubricant to enable the formation of an effective eutectic film during the subsequent autoclave cycle reaches, but does not go beyond, the rotor assembly during each application prior to sterilization.

SUMMARY OF THE INVENTION

Set forth below is a brief summary of the invention which achieves the foregoing and other objects and provides the foregoing and hereafter stated benefits and advantages in accordance with the structure, function and results of the present invention as embodied and broadly described herein. Applicant's invention includes independently both the apparatuses and the methods described herein which achieve the objects and benefits of the present invention. Both formats of the invention are described below, and it is applicant's intention to claim both formats even though from time to time below for purposes of clarity and brevity applicant will use either one or the other format to describe various aspects and features of the invention.

One aspect of the invention is a dental handpiece lubricant dispenser which includes a housing, a pump supported on the housing having inlet and outlet ports, the inlet port coupled to a lubricant supply and the outlet port coupled to a tube having an outlet opening, for delivering a predetermined amount of the lubricant during an activated cycle of the pump, an actuator supported on the housing adapted to be coupled to a power supply, and when cycled causing the pump to deliver a predetermined amount of the lubricant through the outlet port and tube to the outlet opening, and a switch which is independently selectable for cycling the actuator to activate only the active cycle of the pump.

A further feature of this aspect of the invention include he actuator is the actuator is a spring biased solenoid and the pump is a piston-diaphragm type.

A further feature of this aspect of the invention include he actuator is the actuator is a timer circuit with relay and the pump is a motor driven type.

Further features of this aspect of the invention are the active cycle of the pump is activated without also activating a cleaning cycle or a purging cycle, the active cycle of the pump is about one second in duration, the predetermined amount of lubricant which is delivered is in the range of about ⅛ to ½ cc, the lubricant comprises about 90% by volume of a liquid hydrocarbon and about 10% by volume of a lubricant enhancer and corrosion inhibitor, the liquid hydrocarbon is a pharmaceutical grade mineral oil and the lubricant enhancer and corrosion inhibitor is NNL-690, the about 90% by volume of a liquid hydrocarbon includes the range of 80% to 97% by volume and the about 10% by volume of a lubricant enhancer and corrosion inhibitor includes the range of 3% to 20% by volume, the cycle has a duration which is adjustable and controls the predetermined amount of lubricant delivered by the pump, the predetermined amount of the lubricant is delivered during an activated cycle of the pump at a pressure of about 2.6 psi into the air intake hole of the handpiece while holding the handpiece upside down so as to assure that a sufficient supply of the lubricant to enable the formation of an effective eutectic film during a subsequent sterilization step reaches and remains in a rotor assembly of the handpiece, and, an adaptor may be secured on the outlet of the tube having an elongated nozzle for dispensing the lubricant well down into the air intake hole of the handpiece to assure delivery of the maximum amount of the predetermined amount of lubricant as near as possible to the rotor assembly of the handpiece.

The dispenser of the present application has no cleaning function or purpose whatsoever. The dispenser of the present application is used solely for dispensing lubricating oil prior to sterilization, or, as described in greater detail below, for post sterilization lubrication if a separate dispensing mechanism is provided for that function. A totally independently selectable purge function for use solely after sterilization or after post-sterilization lubrication may be provided as an additional option to clear excess oil in the handpiece, as described in greater detail below.

The advantages of the invention are:
1. Fast dispensing of the dose amount.
2. Simple dispensing of the dose amount, just push a button.
3. Accurate dispensing of a measured dose amount (i.e., ⅛–½ ccs).
4. Inexpensive dispensing operations, the estimated retail price being ⅙th of prior art units which perform a similar function.
5. Enabled use of lubricant enhancer and corrosion inhibitor type lubricants, such as, Steri-Lube™ lubricant, for pre-sterilization lubrication with promised vastly improved effectiveness in extending the life of the handpieces.
6. Metered dispensing of said Steri-Lube™ type lubricant under such circumstances (2.6 psi while holding the handpiece upside down and using a needle nosed tip) as to assure that a sufficient supply of said lubricant to enable the formation of an effective eutectic film during the subsequent autoclave cycle reaches, but does not go beyond, the rotor assembly during each application prior to sterilization.
7. Vastly extended effectiveness of the lubricant in the protection of the dental handpiece as a result of the sterilization process.

DETAILED DESCRIPTION OF THE INVENTION

1. The Motorless Solenoid Actuated Pump Embodiment

Figure 8:
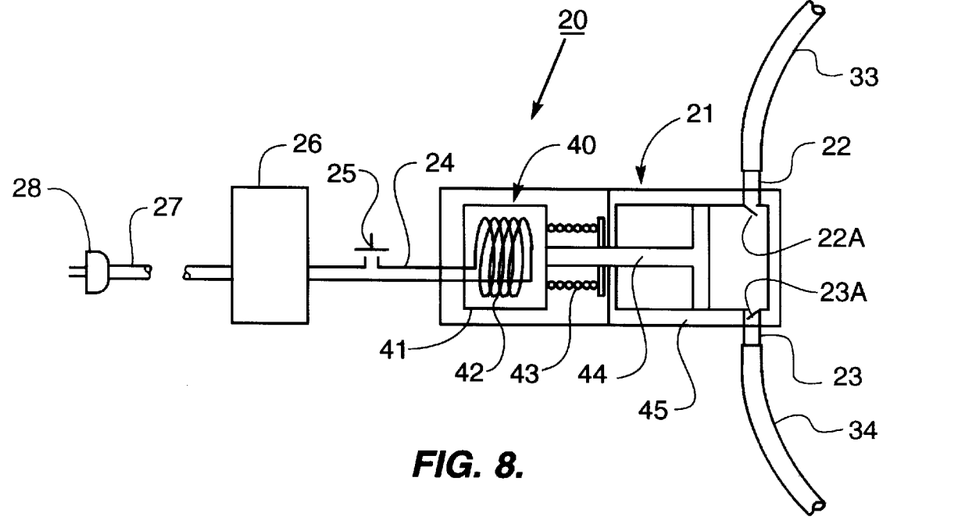
FIG. 8 is a schematic view of a first preferred embodiment of the pump assembly of the present invention showing the pump, the pump actuator assembly, the actuator trigger, the transformer, and the power cord of the present invention.

As seen in FIG. 8 a first preferred embodiment of the present invention is a motorless solenoid actuated pump dispenser which includes a pump assembly 20 which includes a pump 21 having a piston 44 in a housing 45 having an inlet port 22 and inlet port check valve 22A coupled to an inlet tube 33 and an outlet port 23 and outlet port check valve 23A coupled to an outlet tube 34. The check valves 22A, 23A enable the pump to maintain its prime.

A pump actuator assembly 40 includes a solenoid 41 which has a coil 42 surrounding the extended portion of the stem of the piston 44, and a spring 43 mounted between the solenoid 41 and the piston 44.

Power is supplied to the pump actuator assembly 40 of the pump assembly 20 through DC jack 24, transformer assembly 26, power cord 27 and plug 28, from a standard AC external power supply upon actuation of momentary actuator trigger button switch 25 which is connected in the 12VDC line to the actuator coil.

The external power supply is a standard 120–240VAC source and is reduced to 12–24VDC by the transformer 25.

a. Operation

Figure 7:
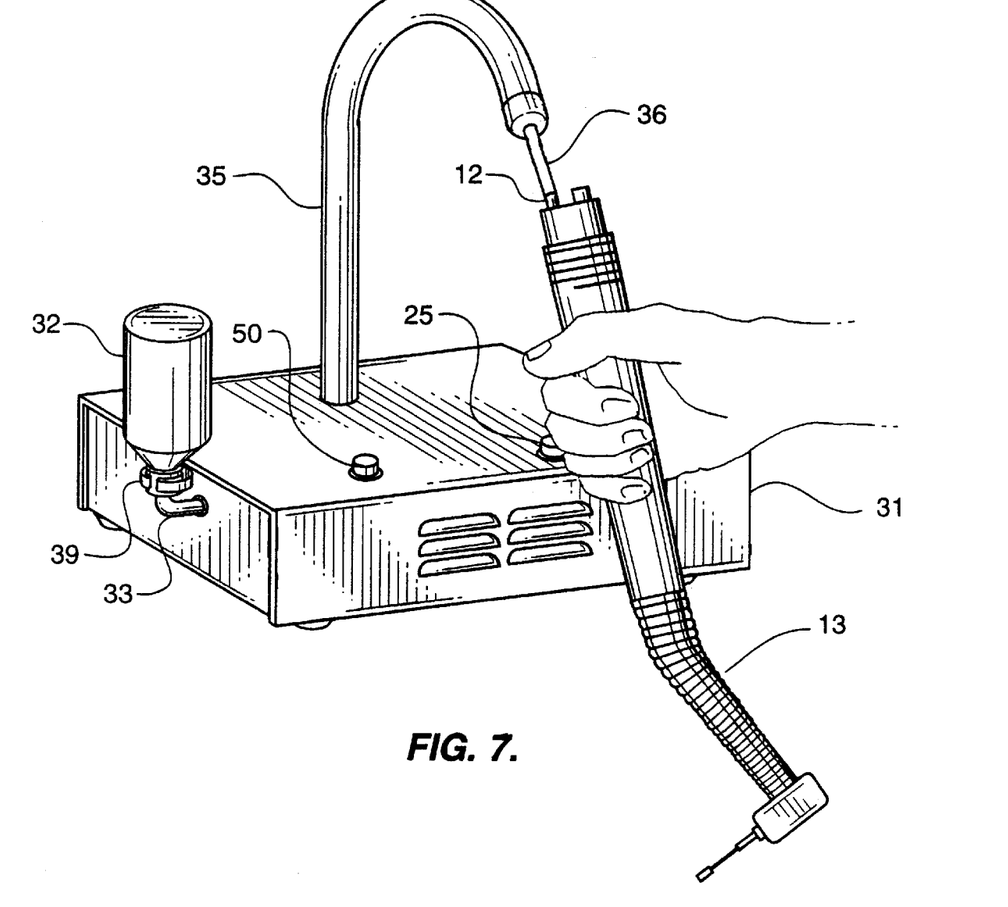
FIG. 7 is a perspective view of one embodiment of the present invention showing the lubricant being automatically pumped into the air intake hole of the handpiece.

Depressing the button switch 25 triggers actuator 40 by energizing the coil 42 of solenoid 41 which pulls the diaphragm piston 44 to the left (FIG. 8) in cylinder housing 45, sucking lubricant 11 from supply bottle 32 through tube 33 and inlet port 22 and check valve 22A and into the pump cylinder 45. When the trigger button 25 is released, solenoid 41 is de-energized and spring 43 pushes piston 44 to the right to its original position forcing the lubricant out of the cylinder and dispensing a measured dose of lubricant 11 past check valve 23A, out port 23 and tube 34, up neck 35, out needle adaptor 36, and into the air intake hole 12 of handpiece 13 (FIG. 7). The cycle is ready to be repeated.

In this embodiment of the invention, there is no motor needed to drive the pump. The solenoid does the job. The amount of the dose is fixed and not variable. Of course, the amount of the dose is a function of the size of the various components including the size of the cylinder, the size of the tubes and tube connectors, and the length of the stroke of the piston. While no adjustment to the piston stroke is shown in FIG. 8, such an adjustment could be added if desired by adding stroke limiters to vary or improve accuracy of the dose. Additionally, stepper linear actuators may be used to replace the solenoids to further improve accuracy and increase the flow rate.

Applicant has found that a working example of a pump assembly of the present invention described in this embodiment is a pump made by Gorman-Rupp Industries of Deliville Ohio 44813 which has the following specifications:

1. Flow Rate: 50 to 250 microliters per stroke (500 microliters per stroke possible utilizing a linear actuator.
2. Pressure: 6' total head (2.6 psi).
3. Fluid Viscosity: up to 300 centistokes.
4. Fluid temperature: 200° F. (93° C.) max.
5. Duty cycle: 1 cycle/sec. max. (½ sec. on; ½ sec. off).
6. Accuracy: +/–10% stroke-to-stroke (+/–2 microliters with linear actuator).
7. Tubing connectors: ³⁄₁₆ in. (5 mm).

Applicant prefers the above embodiment because the design is simple and efficient. The pump is quick, very inexpensive, and the fixed displacement of the pump is just the right amount for applicant's application. Accordingly, there is great reliability, too, and the savings can be passed on to the customer.

b. The Motor Driven Pump Control Circuit Actuated Embodiments

Figure 9:
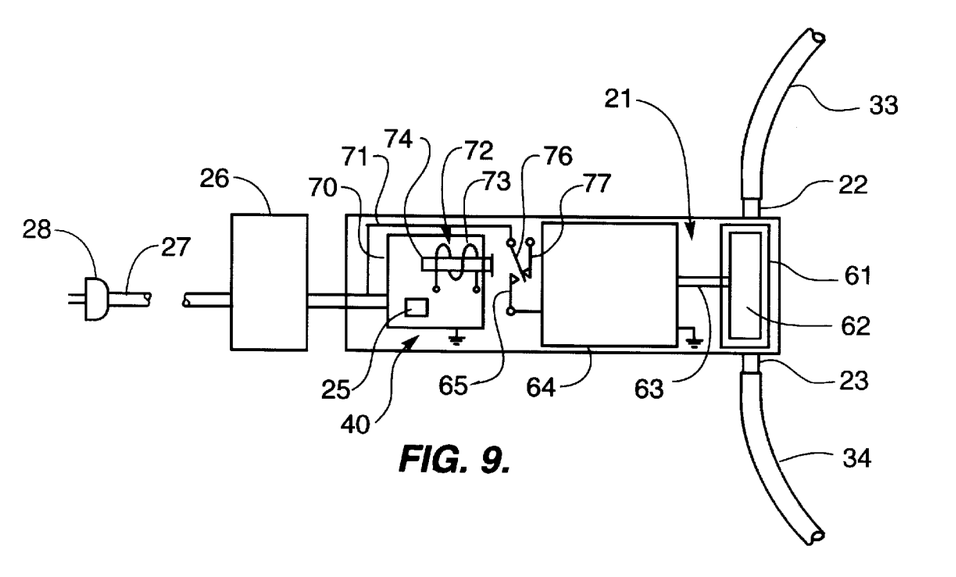
FIG. 9 is a schematic view of a second embodiment of the pump assembly of the present invention showing the pump, the pump actuator assembly, the actuator trigger, the transformer, and the power cord of the present invention.
Figure 10:
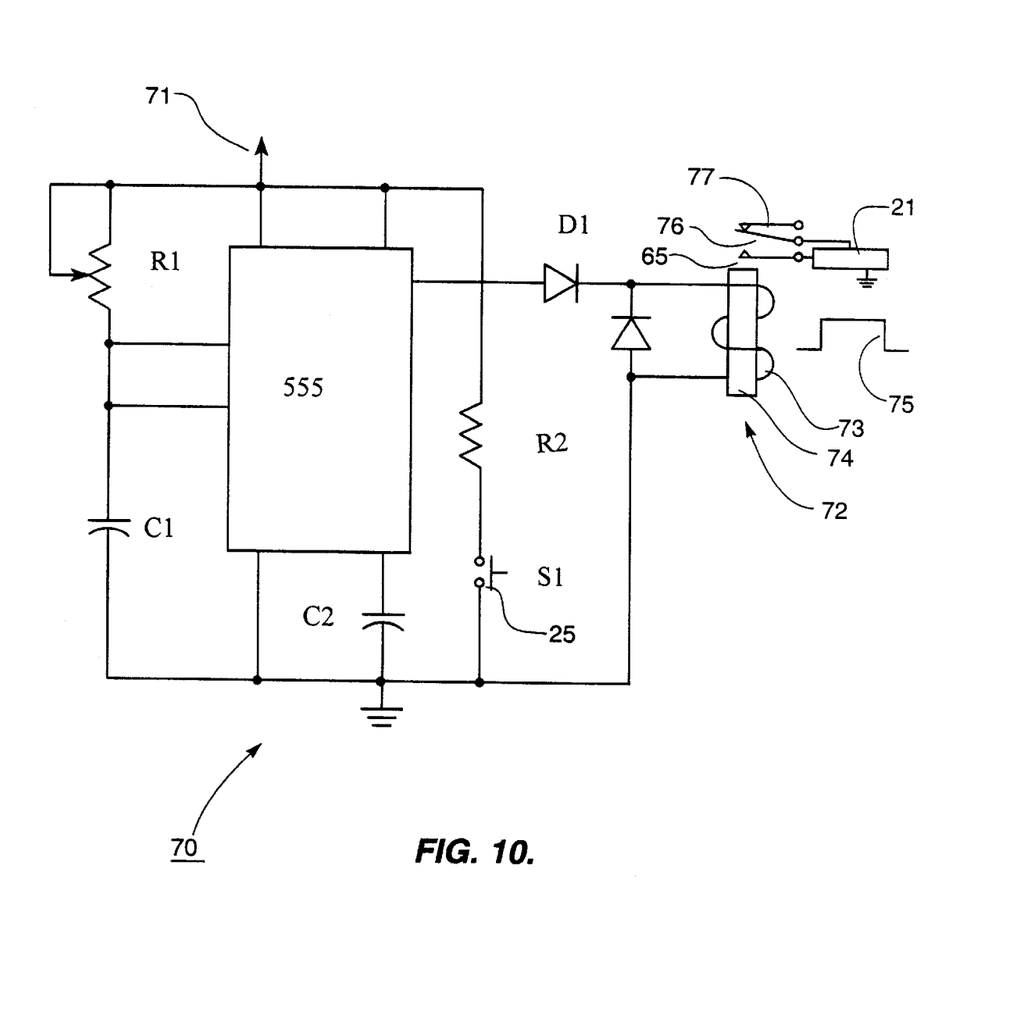
FIG. 10 is a diagram of the control circuit of FIG. 9 which controls the operation of the pump shown in this embodiment of the present invention which uses a peristaltic or gear pump.

As seen in FIGS. 9, 10 a second embodiment of the present invention is a motor driven, control circuit actuated dispenser. This embodiment may utilize any one of several different types of motor driven 12–24VDC miniature pumps, including without limitation, a peristaltic pump, or a gear pump. A peristaltic pump is controlled by a basic single-shot timer circuit, such as actuator assembly control circuit 70 described in greater detail below, which activates the pump for the predetermined period required to dispense a predetermined amount of ccs of dental handpiece lubricant. A gear pump requires check valves to prevent backflow into the pump and to maintain the pump's prime and also requires a timer circuit.

One working example of the motor driven embodiments referred to above as seen in FIG. 9, includes a pump assembly 20 which includes a pump 21 having a housing 61 for an impeller 62 driven by shaft 63 attached to motor 64 having a 12VDC power terminal 65. Also shown is pump actuator assembly 40 which includes a control circuit 70 having a 12VDC power input supply 71 coupled to a relay 72 having a coil 73 surrounding a metal bar 74. The 12 volt supply line is coupled to the movable terminal 76 which in the non-activated position is connected to terminal 77 and in the energized state is coupled to the 12VDC terminal 65 of the motor 64.

Pump actuator trigger button 25 (S1 in FIG. 10) is coupled to control circuit 70 of pump actuator assembly 40.

a. Operation

Shown in FIG. 10 is a conventional circuit diagram for controlling instruments which use a conventional integrated timer circuit No. 555 available at any Radio Shack™ store. Mims, "Engineer's Mini-Notebook 555 Circuits", (Silicon Concepts, 3rd Ed., 5th Printing 1997). Pump actuator trigger switch 25 (S1) is momentarily closed sending a voltage pulse of predetermined duration 75 to coil 73 of relay 72 thereby activating the timing cycle. Pulse 75 energizes bar 74 which pulls the movable terminal 76 into contact with the terminal 65 of the pump motor 64 turning on the motor for the duration of pulse 75. When the motor 64 is running, impeller 62 sucks lubricant 11 from supply bottle 32 through tube 33 and inlet port 22 and into the housing 61 and out port 23 and tube 34, up neck 35, out needle adaptor 36, and into the air intake hole 12 of handpiece. The duration of pulse 75 is controlled by the time constant of the circuit which is set by rheostat R1 in series with C1 which sets the duration of the timed cycle controlling the duration of the period during which the motor is running, thereby adjustably controlling the amount of lubricant dispensed. At the end of the pulse 75, the motor 64 shuts down and is ready for the next cycle. C2 is a small capacitor to ground which prevents false triggering of the pump. D2 absorbs voltage generated by the pump coil when the pump is turned off.

Thus, as seen above, when a peristaltic or gear pump is used, the momentary push button 25 activates the timer circuit 70 for the predetermined amount of time which activates the pump for that same amount of time. In addition, when a gear pump is used, check valves (as shown in FIG. 8) must be provided to prevent backflow and keep the prime of the pump.

In the embodiment of FIGS. 9, 10, the amount of the dose is primarily a function of the duration of the period during which the pump motor is running and that period is adjustable to provide any desired predetermined dose of lubricant.

The pumps in this embodiment are more expensive than in the preferred embodiment discussed above.

c. The Dispenser Fixture

Figure 3:
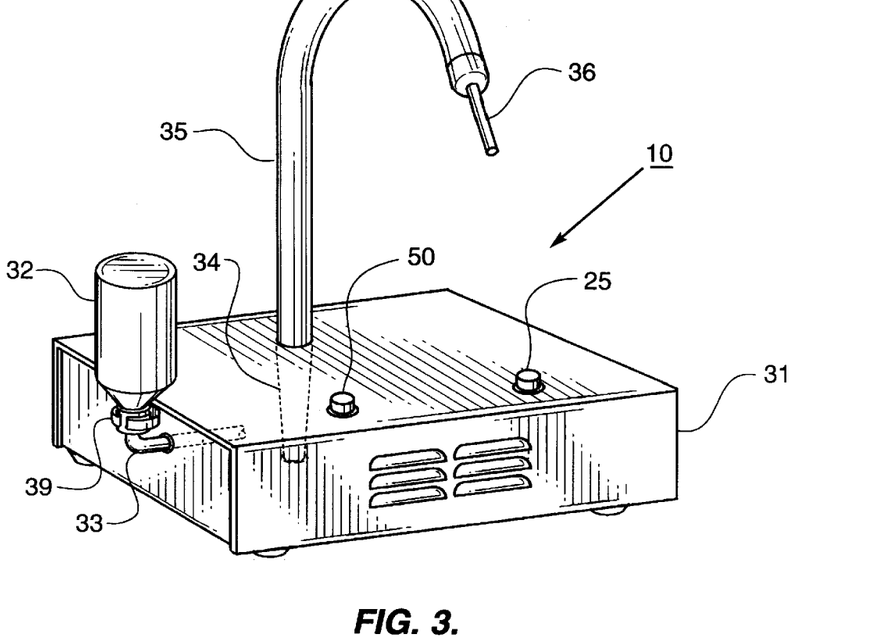
FIG. 3 is a perspective of the dental handpiece lubricant dispenser of the present invention.
Figure 4:
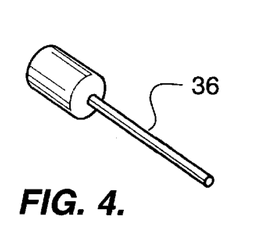
FIGS. 4, 5, 6 are perspective views of adapters which accommodate dental handpieces made by different manufacturers.

As seen in FIG. 3 the present invention further includes a fixture for conveniently dispensing the lubricant which includes the housing assembly 30. This assembly includes a housing 31 which preferably is a simple rectangular enclosure made of sheet metal or plastic. Disposable lubricant supply bottle 32 is mounted in resilient holder 39 on the housing and is connected to the pump inlet via tube 33. The supply bottle 32 is closed by a tapered cap that screws on the bottle. A female fitting is outfitted on the tube to mate with the tapered cap. The holder 39 can accommodate different size bottles that are used in the industry.

The pump assembly 21 is mounted within the housing 31 such that trigger button 25 projects through the top surface of the housing for easy access and with the power cord 13 and plug 14 extending through an opening in a side wall of the housing (not shown). Outlet port 23 is connected by tube 34 to rigid outlet tube 35 ("goose neck") which extends upwardly from the top surface of the housing and then turns downwardly and outwardly, terminating in a threaded outlet to which is secured a needle nosed adaptor 36 adapted to service a handpiece 13 of the type seen in FIGS. 1, 7 which takes the lubricant down the air intake hole with the handpiece held upside down as seen in FIG. 7

Figure 5:
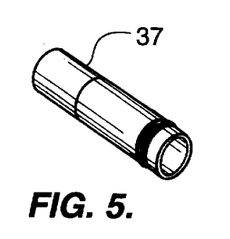
Figure 6:
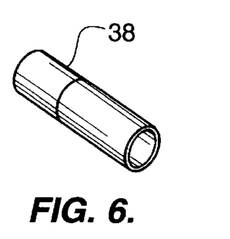

Additional adaptors 37, 38 are shown in FIGS. 5, 6 to accommodate handpieces made by other manufacturers.

When the lubricating cycle of the dispenser of the present invention is complete, the handpiece can then be sterilized according to the industry standards or the handpiece/sterilizer manufacturers' recommendations for the sterilization process.

When the sterilization cycle of the dispenser of the present invention is complete, the handpiece can then be lubricated again prior to use according to the industry standards or the handpiece/sterilizer manufacturers' recommendations for post-sterilization lubrication.

d. Additional And Optional Features

A further embodiment of the present invention includes a second independent dispensing assembly, including supply bottle, inlet tubing, pump, outlet tubing, neck, and outlet (not shown) for use in post-sterilization lubrication of the handpiece 13. The post-sterilization dispensing outlet must function separately and independently of the pre-sterilization outlet in order to prevent cross contamination and to accommodate the different dispensing amounts and different potential types of lubricant needed for these two separate operations.

Optionally the housing 31 may include a conventional LED (not shown) coupled to the 12VDC power supply which is lit when the pump is operating.

As described in greater detail below, an optional feature of the invention is a purge function which is initiated by pushing momentary actuation push button 50 (FIGS. 3, 7) which also protrudes from the top surface of housing 31. For example, a purger assembly (not shown) would include a purger air valve 50 (FIGS. 3, 7) connected to an independent compressed air supply line (not shown). The purger assembly may include various conventional air couplers and adapters for coupling to the air lines as is well known to those of ordinary skill in the dental art, an air pressure gauge, an air relief valve for relief of pressures which exceed 45 psi (so as not to exceed dental handpiece manufacturers' maximum air pressure recommendations of 45–50 psi).

After the sterilization process is complete, or after the post-sterlization lubrication process is complete, a handpiece may then also be purged of excess lubricant still present in the handpiece. In the preferred embodiment seen in FIGS. 3, 7, a handpiece is purged by inserting it into the purging valve outlet 50 and pressing it downwardly with a little force which unseats the valve air seal and allows compressed air to blow through the air intake hole 12 of the handpiece 13 to remove any excess oil from the handpiece. Compressed air will continue to be purged through the handpiece until the handpiece is removed from the valve 50, reseating the air valve seal. The pressure gauge lets the operator monitor line air pressure during the purging operation.

The foregoing description of a preferred embodiment and best mode of the invention known to applicant at the time of filing the application has been presented for the purposes of illustration and description. It is not intended to be exhaustive or to limit the invention to the precise form disclosed, and obviously many modifications and variations are possible in the light of the above teaching. The embodiment was chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

I claim:

1. A dental handpiece lubricant dispenser having an air intake hole comprising:
   (a) a housing having a surface;
   (b) a holder on said housing for replaceably receiving a lubricant supply container;
   (c) delivery means on said housing having an inlet port, a supply chamber and an outlet port, said inlet port connectable to said lubricant supply;
   (d) an outlet tube extending upwardly from said surface connected with said outlet port and having an outlet opening terminating at a downwardly turned gooseneck spaced above said surface and alignable with the intake hole of the handpiece; and
   (e) an actuator supported on the housing adapted to be coupled to a power supply when activated causing the delivery means to deliver a predetermined amount of lubricant through the outlet port and tube to the outlet port and tube to the outlet opening whereby the user may position a handpiece inverted with the intake hole aligned with the outlet opening and deliver a measured amount of lubricant by activating the actuator.

2. The dispenser of claim 1 whereby said delivery means comprises a pump.

3. The dispenser of claim 1 having a purger air valve having an air discharge on said surface, said air valve connectable to a compressed air source and actuable by engaging a handpiece therewith.

4. A method of lubricating a dental handpiece of the type having an air intake comprising the steps of:
   (a) providing lubricant delivery means associated with a housing for delivering a predetermined amount of lubricant to an outlet tube extending from a surface of said housing and terminating at a downwardly turned outlet spaced above said housing;
   (b) providing a holder on said housing for receiving a container of lubricant;
   (c) connecting said lubricant container to said delivery means;
   (d) manually placing said handpiece in an inverted lubricating position with the air intake aligned with said outlet tube; and (e) activating said delivery means to deliver said predetermined amount of lubricant to said handpiece while manually maintaining said handpiece in said lubricating position.

5. The method of claim 4 wherein said outlet is a gooseneck positioned above said surface providing clearance so the user may manually position the handpiece in a generally vertically inverted position aligned with said outlet.

6. The method of claim 4 including the further step providing an air pressure outlet on said surface and manually engaging said handpiece with said air outlet to induce a purging flow of air to said handpiece when said handpiece and valve are engaged.

7. The method of claim 4 further including the step sterilizing the handpiece.

8. The dispenser of claim 1 further comprising:
   the actuator is a spring biased solenoid and the pump is a piston-diaphragm type.

9. The dispenser of claim 1 further comprising:
   the actuator is a timer circuit with relay and a motor driven pump.

10. The dispenser of claim 1 wherein the lubricant comprises about 90% by volume of a liquid hydrocarbon and about 10% by volume of a lubricant enhancer and corrosion inhibitor.

11. The dispenser of claim 10 wherein the liquid hydrocarbon is a pharmaceutical grade mineral oil and the lubricant enhancer and corrosion inhibitor is NNL-690.

12. The dispenser of claim 10 wherein the about 90% by volume of a liquid hydrocarbon includes the range of 80% to 97% by volume, and the about 10% by volume of a lubricant enhancer and corrosion inhibitor includes the range of 3% to 20% by volume.

13. The dispenser of claim 1 wherein the duration of the operation actuator is adjustable and controls the predetermined amount of lubricant delivered.

14. The dispenser of claim 1 wherein the predetermined amount of the lubricant is delivered at a pressure of about 2.6 psi into the air intake hole of the handpiece while holding the handpiece upside down so as to assure that a sufficient supply of the lubricant to enable the formation of an effective eutectic film during a subsequent sterilization step reaches and remains in a rotor assembly of the handpiece.

15. The dispenser of claim 14 further comprising an adaptor secured on the outlet of the tube having an elongated nozzle for dispensing the lubricant well down into the air intake hole of the handpiece to assure delivery of the maximum amount of the predetermined amount of lubricant as near as possible to the rotor assembly of the handpiece.

16. The method of claim 4 further comprising the step of:
   cycling a spring biased solenoid to actuate said delivery means.

17. The method of claim 4 further comprising the step of:
   cycling a timer circuit with relay to-activate said delivery means.

18. The method of claim 4 further comprising the step of:
   delivering a predetermined amount of lubricant in the range of about 1/8 to 1/2 cc.

19. The method of claim 4 further comprising the step of:
   delivering a lubricant comprising about 90% by volume of a liquid hydrocarbon and about 10% by volume of a lubricant enhancer and corrosion inhibitor.

20. The method of claim 19 further comprising the step of:
   delivering a lubricant wherein the about 90% by volume of a liquid hydrocarbon is a pharmaceutical grade mineral oil and the lubricant enhancer and corrosion inhibitor is NNL-690.

21. The method of claim 19 further comprising the step of:
   delivering a lubricant wherein the about 90% by volume of a liquid hydrocarbon includes the range of 80% to 97% by volume, an the about 10% by volume of a lubricant enhancer and corrosion inhibitor includes the range of 3% to 20% by volume.

22. The method of claim 4 further comprising the step of:
   delivering the predetermined amount of the lubricant at a pressure of about 2.6 psi into the air intake hole of handpiece while holding the handpiece upside down so as to assure that a sufficient supply of the lubricant to enable the formation of an effective eutectic film during a subsequent sterilization step reaches and remains in a rotor assembly of the handpiece.

23. The method of claim 22 further comprising the step of:
   securing an actuator to the outlet of the tube having an elongated nozzle and dispensing the lubricant well down into the air intake hole of the handpiece to assure delivery of the maximum amount of the predetermined amount of lubricant as near as possible to the rotor assembly of the handpiece.

24. The method of claim 4 further comprising the step of:
   sterilizing the handpiece, and then purging the handpiece.

25. The method of claim 4 further comprising the step of:
   sterilizing the handpiece, lubricating the handpiece, and then purging the handpiece.

\* \* \* \* \*